United States Patent
Hayakawa et al.

(10) Patent No.: US 12,421,093 B2
(45) Date of Patent: Sep. 23, 2025

(54) CAP STERILIZATION DEVICE AND CONTENT FILLING SYSTEM

(71) Applicant: Dai Nippon Printing Co., Ltd., Tokyo (JP)

(72) Inventors: Atsushi Hayakawa, Tokyo (JP); Yoshinori Satou, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 136 days.

(21) Appl. No.: 17/755,979

(22) PCT Filed: Dec. 2, 2020

(86) PCT No.: PCT/JP2020/044944
§ 371 (c)(1),
(2) Date: May 13, 2022

(87) PCT Pub. No.: WO2021/112152
PCT Pub. Date: Jun. 10, 2021

(65) Prior Publication Data
US 2022/0402740 A1    Dec. 22, 2022

(30) Foreign Application Priority Data
Dec. 4, 2019 (JP) .................. 2019-219714

(51) Int. Cl.
*A61L 2/18* (2006.01)
*A61L 2/20* (2006.01)
(Continued)

(52) U.S. Cl.
CPC .............. *B67B 3/003* (2013.01); *B67C 7/004* (2013.01); *B67C 7/0086* (2013.01); *B67C 2007/006* (2013.01); *B67C 2007/0066* (2013.01)

(58) Field of Classification Search
CPC .............. B67B 3/003; B67C 2007/006; B67C 2007/0066
See application file for complete search history.

(56) References Cited

U.S. PATENT DOCUMENTS 3,623,594 A * 11/1971 Ravn .................... B65G 47/145
198/399
3,833,339 A * 9/1974 Pacilio .................... B67B 3/003
422/119

(Continued)

FOREIGN PATENT DOCUMENTS

| CN | 109153470 A | 1/2019 |
|---|---|---|
| EP | 2 687 478 A1 | 1/2014 |

(Continued)

OTHER PUBLICATIONS

English translation of the International Preliminary Report on Patentability (Chapter I) dated Jun. 16, 2022 (Application No. PCT/JP2020/044944).

(Continued)

*Primary Examiner* — Thanh K Truong
*Assistant Examiner* — David G Shutty
(74) *Attorney, Agent, or Firm* — BURR PATENT LAW, PLLC (57) ABSTRACT

A cap sterilization device (50) includes an introduction unit (52), a sterilant spraying unit (53) that sprays a sterilant onto a cap (33) supplied from the introduction unit (52), an air-rinsing unit (54) that subjects the cap (33) onto which the sterilant has been sprayed by the sterilant spraying unit (53) to air-rinsing, and a conveyance guide (70) that is disposed to extend successively through the introduction unit (52), the sterilant spraying unit (53), and the air-rinsing unit (54) and along which the cap (33) is conveyed from the introduction unit (52) toward the air-rinsing unit (54). The air-rinsing unit (54) is provided with an air-rinsing nozzle (83) that supplies (Continued)

hot air to the cap (33). The air-rinsing nozzle (83) is disposed such that a distal end (83a) thereof is in front of a proximal end (83b) thereof in a conveying direction of the conveyance guide (70).

5 Claims, 5 Drawing Sheets

(51) Int. Cl.
    *B67B 3/00*     (2006.01)
    *B67C 7/00*     (2006.01)

(56) References Cited

U.S. PATENT DOCUMENTS

| | | | |
|---|---|---|---|
| 3,905,317 A * | 9/1975 | Pacilio | A61L 2/24 422/40 |
| 7,815,877 B2 * | 10/2010 | Krakers | A61L 2/202 422/302 |
| 8,291,680 B2 * | 10/2012 | Silvestri | B67B 3/06 53/500 |
| 8,574,492 B2 * | 11/2013 | Morita | A61L 2/18 134/131 |
| 8,931,239 B2 * | 1/2015 | Evers | B67B 3/003 53/306 |
| 8,945,477 B2 | 2/2015 | Ceci et al. | |
| 2010/0275955 A1 * | 11/2010 | Ueda | A61L 2/07 134/131 |
| 2011/0138740 A1 | 6/2011 | Evers | |
| 2013/0004368 A1 | 1/2013 | Morita et al. | |
| 2017/0057679 A1 * | 3/2017 | Ogawa | A61L 2/08 |
| 2019/0337786 A1 | 11/2019 | Hayakawa et al. | |

FOREIGN PATENT DOCUMENTS

| | | | | |
|---|---|---|---|---|
| EP | 2789574 A1 * | 10/2014 | | B67B 3/003 |
| JP | S63-044429 A | 2/1988 | | |
| JP | H02-010462 U | 1/1990 | | |
| JP | H02-191166 A | 7/1990 | | |
| JP | 06293319 A * | 10/1994 | | B65B 55/10 |
| JP | H06-293319 A | 10/1994 | | |
| JP | 2001-315720 A | 11/2001 | | |
| JP | 2001-341707 A | 12/2001 | | |
| JP | 4408142 B2 | 2/2010 | | |
| JP | 2011-011811 A | 1/2011 | | |
| JP | 2012-500759 A | 1/2012 | | |
| JP | 5443860 B2 | 3/2014 | | |
| WO | 2009/084361 A1 | 7/2009 | | |
| WO | 2010/012334 A1 | 2/2010 | | |
| WO | 2011/111513 A1 | 9/2011 | | |
| WO | WO-2017209185 A1 * | 12/2017 | | A61L 2/18 |

OTHER PUBLICATIONS

Chinese Office Action (Application No. 202080083670.8) dated Mar. 31, 2023 (with English translation) (22 pages).
International Search Report and Written Opinion (Application No. PCT/JP2020/044944) dated Feb. 9, 2021 (with English translation).
Extended European Search Report dated Dec. 12, 2023 (Application No. 20896868.5).

* cited by examiner

CAP STERILIZATION DEVICE AND CONTENT FILLING SYSTEM

TECHNICAL FIELD

The present disclosure relates to a cap sterilization device and a content filling system.

BACKGROUND ART

A sterile filling system (aseptic filling system) that fills a sterilized container (PET bottle) with a sterilized content in a sterile environment and then closes the container with a cap is known. More specifically, in the sterile filling system, a molded container is supplied to the sterile filling system, and an aqueous hydrogen peroxide solution, which serves as a sterilant, is sprayed onto the container in the sterile filling system. After that, the sterilant is dried to sterilize the container, and then the container is aseptically filled with a content. In another method, a small amount of sterilant is applied dropwise to an inner surface of the container when the container is molded. Then, the mouth of the container is sealed, and the inner surface of the container is sterilized with vapor of the sterilant (hydrogen peroxide) that is vaporized. The sterilized container is supplied to the sterile filling system, and the outer surface of the container is sterilized in the sterile filling system. Then, the mouth is opened and the container is aseptically filled with a content.

To produce a product by filling a container with a content and closing the container with a cap in the sterile filling system, it is necessary to sterilize the cap as well as the container. Patent Documents 1 to 3 describe examples of a cap sterilization device for sterilizing a cap.

However, it is difficult to increase a conveyance rate at which the cap is conveyed in the cap sterilization device according to the related art. If the conveyance rate of the cap is increased in the cap sterilization device according to the related art, the effect of sterilizing the outer surface of the cap may be reduced. In addition, an increase in the conveyance rate of the cap leads to an increase in the size of the device. Accordingly, the capital investment costs and the costs of chemical agents used for sterilization, thermal energy, or cleaning water will be increased. Also, in recent years, various caps, such as light weight caps and carbonated beverage caps, have been used in sterile filling systems. Therefore, it is desirable not only to perform sterilization in a short time but also to adjust the cap tightening angle and torque in predetermined ranges.

PRIOR ART REFERENCES

Patent Documents

[Patent Document 1] Japanese Unexamined Patent Application Publication No. 6-293319
[Patent Document 2] Japanese Unexamined Patent Application Publication No. 2011-11811
[Patent Document 3] Japanese Unexamined Patent Application Publication No. 2012-500759

An object of the present disclosure is to provide a cap sterilization device and a content filling system in which a cap can be conveyed at a high conveyance rate.

DISCLOSURE OF THE INVENTION

A cap sterilization device according to the present embodiment includes an introduction unit; a sterilant spraying unit that sprays a sterilant onto a cap supplied from the introduction unit; an air-rinsing unit that subjects the cap onto which the sterilant has been sprayed by the sterilant spraying unit to air-rinsing; and a conveyance guide that is disposed to extend successively through the introduction unit, the sterilant spraying unit, and the air-rinsing unit and along which the cap is conveyed from the introduction unit toward the air-rinsing unit. The air-rinsing unit is provided with an air-rinsing nozzle that supplies hot air to the cap, the air-rinsing nozzle being disposed such that a distal end thereof is in front of a proximal end thereof in a conveying direction of the conveyance guide.

In the cap sterilization device according to the present embodiment, the air-rinsing nozzle may be disposed on each side of the conveyance guide.

In the cap sterilization device according to the present embodiment, an angle between the air-rinsing nozzle and the conveying direction of the conveyance guide may be 10° or more and 80° or less when viewed in a direction normal to a plane on which the conveyance guide is disposed.

In the cap sterilization device according to the present embodiment, the cap may be conveyed at a conveyance rate of 100 cpm or more and 1500 cpm or less.

In the cap sterilization device according to the present embodiment, the introduction unit may be provided with an upstream nozzle that discharges a sterilant or cleaning liquid, and the sterilant spraying unit and the air-rinsing unit are successively sterilized or cleaned by the sterilant or the cleaning liquid discharged by the upstream nozzle.

A content filling system according to the present embodiment includes the cap sterilization device according to the present embodiment.

According to the present embodiment, the conveyance rate of the cap can be increased.

DESCRIPTION OF EMBODIMENTS

An embodiment will now be described with reference to FIGS. 1 to 5. FIGS. 1 to 5 illustrate the embodiment. In each of the drawings described below, the same parts are denoted by the same reference signs, and detailed description thereof may be omitted.

(Content Filling System)

A content filling system (sterile filling system, aseptic filling system) according to the present embodiment will be described with reference to FIG. 1.

Figure 1:
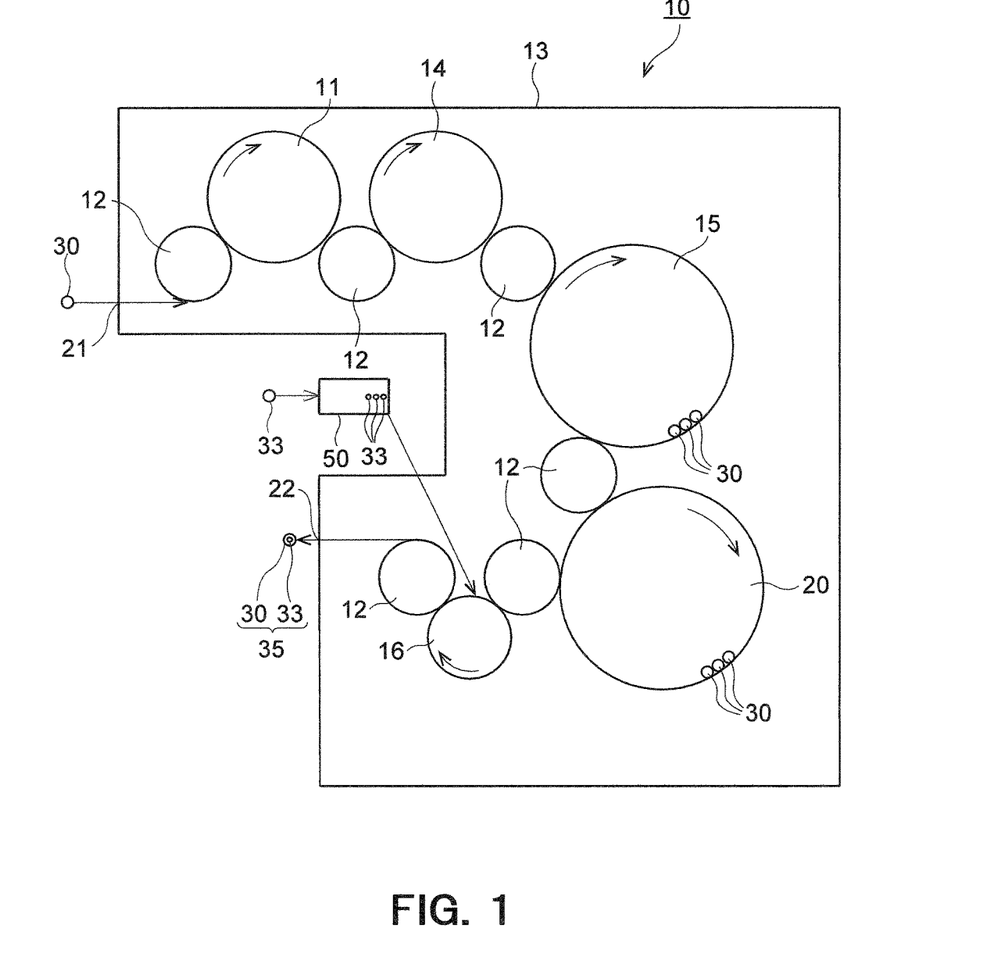
FIG. 1 is a schematic plan view of a content filling system according to an embodiment.

A content filling system 10 illustrated in FIG. 1 is a system for filling bottles (containers) 30 with a content, such as a beverage. The bottles 30 may be produced by performing biaxial stretching blow molding on preforms formed by injection molding of a synthetic resin material. The material of the bottles 30 is preferably a thermoplastic resin, in particular, polyethylene (PE), polypropylene (PP), polyethylene terephthalate (PET), or polyethylene naphthalate (PEN). The containers may each be composed of glass, a can, paper, a pouch, or a composite container thereof. In the present embodiment, it is assumed that the containers are bottles made of a synthetic resin.

As illustrated in FIG. 1, the content filling system 10 includes a bottle supplying unit 21, a sterilization device 11, an air-rinsing device 14, a sterile-water-rinsing device 15, a filling device (filler) 20, and a cap attaching device (capper, a closing-and-capping machine) 16, and a product bottle carry-out unit 22. The bottle supplying unit 21, the sterilization device 11, the air-rinsing device 14, the sterile-water-rinsing device 15, the filling device 20, the cap attaching device 16, and the product bottle carry-out unit 22 are arranged in that order from the upstream side toward the downstream side in a conveying direction of the bottles 30. A plurality of conveying wheels 12 are provided between the sterilization device 11, the air-rinsing device 14, the sterile-water-rinsing device 15, the filling device 20, and the cap attaching device 16 to convey the bottles 30 between these devices.

The bottle supplying unit 21 successively receives empty bottles 30 to be supplied to the content filling system 10 from the outside, and conveys the received bottles 30 to the sterilization device 11.

A bottle molding unit (not illustrated) that molds the bottles 30 by performing biaxial stretching blow molding on preforms may be disposed upstream of the bottle supplying unit 21. Thus, processes of supplying the preforms, molding the bottles 30, filling the bottles 30 with a content, and closing the bottles 30 may be successively performed. In such a case, the preforms, which are small in volume, may be transported from the outside to the content filling system 10 instead of the bottles 30 having a large volume. Therefore, the size of the facility including the content filling system 10 can be reduced.

The sterilization device 11 sterilizes the interiors of the bottles 30 by spraying a sterilant into the bottles 30. The sterilant may be, for example, an aqueous hydrogen peroxide solution. In the sterilization device 11, the aqueous hydrogen peroxide solution having a concentration of 1% by weight or more, preferably 35% by weight, is temporarily vaporized, and then condensed to generate mist or gas. The mist or gas is sprayed onto the inner and outer surfaces of the bottles 30. Since the interiors of the bottles 30 are sterilized with the aqueous hydrogen peroxide solution in the form of mist or gas, the inner surfaces of the bottles 30 are uniformly sterilized.

The air-rinsing device 14 supplies sterile heated air or room temperature air to each bottle 30 to remove foreign matter, hydrogen peroxide, etc. from the bottles 30 while activating the hydrogen peroxide.

The sterile-water-rinsing device 15 receives the bottles 30 sterilized with hydrogen peroxide, which is the sterilant, and cleans the bottles 30 with sterile water at a temperature of 15° C. to 85° C. Thus, the hydrogen peroxide that has adhered to the bottles 30 is rinsed off, and foreign matter is removed.

The filling device 20 fills the bottles 30 with a content sterilized in advance through the mouths of the bottles 30. The filling device 20 introduces the content into the bottles 30 in an empty state. The filling device 20 introduces the content into the bottles 30 while rotating (revolving) the bottles 30. The content may be introduced into the bottles 30 at a room temperature. The content is sterilized by being heated, for example, in advance and then cooled to a room temperature of 3° C. or more and 40° C. or less before being introduced into the bottles 30. The content with which the bottles 30 are filled by the filling device 20 may be, for example, a beverage, such as a tea-based beverage or a milk-based beverage.

The cap attaching device 16 closes the bottles 30 that have been filled with the content by the filling device 20 by attaching caps 33 to the mouths of the bottles 30. The cap attaching device 16 closes the mouths of the bottles 30 with the caps 33 to seal the bottles 30 and prevent entrance of external air and microbes into the bottles 30. The cap attaching device 16 attaches the caps 33 to the mouths of the bottles 30 filled with the content while rotating (revolving) the bottles 30. Thus, product bottles 35 are obtained by attaching the caps 33 to the mouths of the bottles 30.

The caps 33 are sterilized in advance by a cap sterilization device 50. The cap sterilization device 50 is, for example, disposed outside a sterile chamber 13 (described below) and near the cap attaching device 16. The caps 33 that are conveyed into the cap sterilization device 50 from the outside are accumulated in advance, and then conveyed toward the cap attaching device 16 in a line. While the caps 33 are being conveyed toward the cap attaching device 16, hydrogen peroxide in the form of mist or gas is blown against the inner and outer surfaces of the caps 33. After that, the caps 33 are dried with hot air and sterilized. The structure of the cap sterilization device 50 will be described below.

The product bottle carry-out unit 22 successively conveys the product bottles 35 including the caps 33 attached by the cap attaching device 16 to the outside of the content filling system 10.

The content filling system 10 includes the sterile chamber 13. The sterile chamber 13 houses the sterilization device 11, the air-rinsing device 14, the sterile-water-rinsing device 15, the filling device 20, and the cap attaching device 16 described above. The content filling system 10 may be composed of, for example, a sterile filling system. In such a case, the interior of the sterile chamber 13 is maintained in a sterile state.

Alternatively, the content filling system 10 may be a high-temperature filling system that fills with the content at a high temperature of 85° C. or more and less than 100° C. Alternatively, the content filling system 10 may be a medium-temperature filling system that fills with the content at a medium temperature of 55° C. or more and less than 85° C.

(Cap Sterilization Device)

Figure 2:
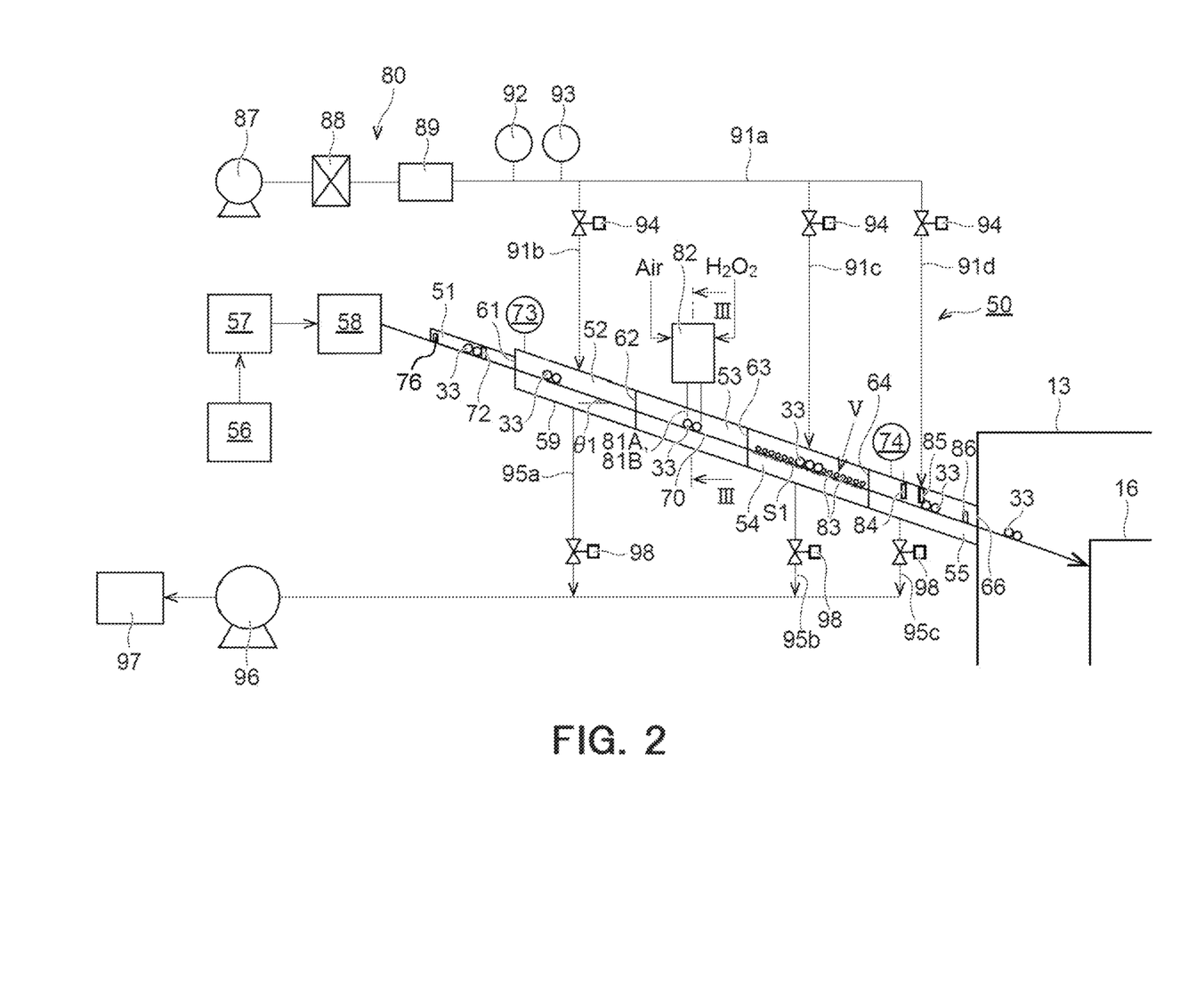
FIG. 2 is a schematic front view of a cap sterilization device according to the embodiment.

The structure of the above-described cap sterilization device 50 will now be described with reference to FIG. 2. FIG. 2 is a schematic front view of the cap sterilization device 50 according to the present embodiment. The upward and downward directions in FIG. 2 respectively correspond to vertically upward and downward directions.

As illustrated in FIG. 2, the cap sterilization device 50 includes a cap introduction unit 51, an introduction chamber (introduction unit) 52, a sterilant spraying chamber (sterilant spraying unit) 53, an air-rinsing chamber (air-rinsing unit) 54, and a cleaning chamber (cleaning unit) 55. The cap introduction unit 51, the introduction chamber 52, the sterilant spraying chamber 53, the air-rinsing chamber 54, and the cleaning chamber 55 are arranged in that order in a conveying direction of caps 33 from an upper location toward a lower location in the vertical direction. The chambers 52, 53, 54, and 55 are disposed in a tubular body 59.

The cap introduction unit 51 and the introduction chamber 52 are separated from each other by a partition wall 61 provided therebetween. Similarly, the introduction chamber 52 and the sterilant spraying chamber 53 are separated from each other by a partition wall 62. The introduction chamber 52 and the air-rinsing chamber 54 are separated from each other by a partition wall 63. The sterilant spraying chamber 53 and the air-rinsing chamber 54 are separated from each other by a partition wall 64. The air-rinsing chamber 54 and the cleaning chamber 55 are separated from each other by a partition wall 65. The cleaning chamber 55 and the sterile chamber 13 are separated from each other by a partition wall 66. It is not necessary that all of the chambers 52, 53, 54, and 55 be provided with the partition walls 61 to 66 disposed therebetween, and at least one or more of the partition walls 61 to 66 are preferably provided. In addition, although the chambers 52, 53, 54, and 55 are partitioned from each other in the form of independent rooms in the present embodiment, the chambers 52, 53, 54, and 55 are not limited to this. The introduction unit 52, the sterilant spraying unit 53, the air-rinsing unit 54, and the cleaning unit 55 may instead be configured such that at least one thereof is not partitioned in the form of a room (does not constitute a chamber).

These partition walls 61, 62, 63, 64, 65, and 66 prevent gas, water, or the like from flowing between the chambers 52, 53, 54, and 55, and serve to stabilize the pressures in the chambers 52, 53, 54, and 55. The partition walls 61, 62, 63, 64, 65, and 66 each have an opening large enough to allow the caps 33, for example, to pass therethrough. The openings have a minimum size, for example, about the size of one cap 33, to prevent variations in the pressures in the chambers 52, 53, 54, and 55.

A hopper 56, a sorter 57, and a cap inspection device 58 are disposed upstream of the cap introduction unit 51. A large number of caps 33 are randomly charged into the hopper 56 from the outside. The sorter 57 aligns the caps 33 that have been randomly charged into the hopper 56 in one or more lines, and conveys the caps 33 from a lower location toward an upper location in the vertical direction. The cap inspection device 58 inspects the shapes, for example, of the caps 33 and discharges the caps 33 that have failed the inspection. The caps 33 that have passed the inspection are conveyed in a line toward the cap introduction unit 51.

Figure 3:
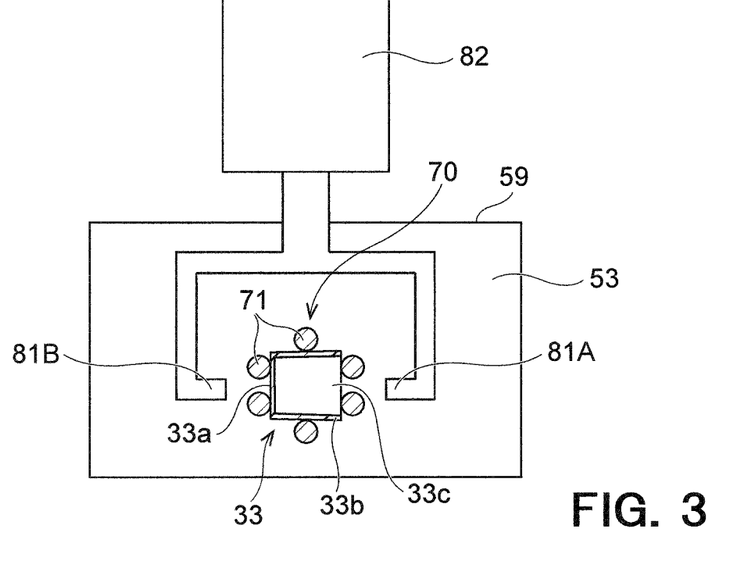
FIG. 3 is a schematic sectional view of a sterilant spraying chamber included in the cap sterilization device according to the embodiment (sectional view taken along line III-III in FIG. 2).

Well-known caps that are substantially circular in plan view and have an opening in an inner surface are used as the caps 33. As illustrated in FIG. 3, each cap 33 has a circular top surface 33*a* and a cylindrical side surface 33*b* that extends from the top surface 33*a* and has an opening 33*c*. The caps 33 may be made of a thermoplastic resin, such as high-density polyethylene (HDPE), polypropylene (PP), or biodegradable plastic. The caps 33 may be general bottle caps, but may also be composite bottle caps or sport bottle caps.

A conveyance guide (chute) 70 along which the caps 33 are conveyed in a line is provided in the cap introduction unit 51 and the chambers 52, 53, 54, and 55. The conveyance guide 70 is inclined and disposed to extend successively through the cap introduction unit 51, the introduction chamber 52, the sterilant spraying chamber 53, the air-rinsing chamber 54, and the cleaning chamber 55. The caps 33 are conveyed along the conveyance guide 70 by their own weight from the cap introduction unit 51 and the introduction chamber 52 toward the air-rinsing chamber 54 and the cleaning chamber 55 through the sterilant spraying chamber 53.

As illustrated in FIG. 3, the conveyance guide 70 includes, for example, a plurality of straight rails 71 (six rails 71 in this example). Each cap 33 is oriented so that the top surface 33*a* thereof faces sideways (in other words, so that the top surface 33*a* is parallel to the vertical direction). Each rail 71 is composed of a rod-shaped body having a circular shape in cross section. The rails 71 are arranged so that two (at least one) rails 71 face the top surface 33*a* of the cap 33, two (at least one) rails 71 face the opening 33*c* in the cap 33, one rail 71 is disposed above the cap 33, and another rail 71 is disposed below the cap 33. The cap 33 is conveyed such that the cylindrical side surface 33*b* rolls (rotates) along the rail 71 disposed below the cap 33. The other rails 71 guide the cap 33 to maintain the orientation of the cap 33. In this case, a space small enough to prevent the cap 33 from falling is formed in a region surrounded by the rails 71, and the cap 33 is conveyed through this space.

As illustrated in FIG. 2, the conveyance guide 70 extends substantially straight overall, and the caps 33 are moved by their own weight from an upper location toward a lower location along the rails 71 of the conveyance guide 70. An angle θ1 between the conveyance guide 70 and the horizontal plane may be 5° or more and 80° or less. In this case, the angle θ1 is constant in the cap introduction unit 51 and the chambers 52, 53, 54, and 55. However, the angle θ1 may vary depending on the locations.

The structures of the cap introduction unit 51 and each of the chambers 52, 53, 54, and 55 will now be further described.

Referring to FIG. 2, the caps 33 are introduced into the cap introduction unit 51 from the cap inspection device 58. The cap introduction unit 51 is provided with a cap movement controller 72 that controls the movement of the caps 33 along the conveyance guide 70. The cap movement controller 72 allows the caps 33 to move or stops the movement of the caps 33. The cap movement controller 72 may be a stopper capable of being opened and closed, or a segmented wheel that rotates. In the case where the cap movement controller 72 is a stopper, when, for example, the cap movement controller 72 temporarily stops the caps 33 on the conveyance guide 70, the caps 33 accumulate on the conveyance guide 70 in a region above the cap movement controller 72. Then, when the cap movement controller 72 is opened, the caps 33 that have accumulated pass the cap movement controller 72 and move toward the introduction chamber 52. A sensor 76 may be provided on the conveyance guide 70 at a location above the cap movement controller 72, and be used to determine the number of caps 33 that have accumulated on the conveyance guide 70. When the cap movement controller 72 that controls the movement of the caps 33 along the conveyance guide 70 is provided, the rate at which the caps 33 are conveyed through the chambers 52, 53, 54, and 55 can be maintained in a certain range.

The caps 33 are supplied from the cap introduction unit 51 to the introduction chamber 52 along the conveyance guide 70. The introduction chamber 52 is disposed below the cap introduction unit 51. Sterile hot air is supplied to the introduction chamber 52 from a hot air supplier 80. The temperature of the sterile hot air is, for example, 40° C. or more and 120° C. or less. Accordingly, the temperature in the introduction chamber 52 is maintained at, for example, 30° C. or more and 80° C. or less. Therefore, condensation of sterilant in the introduction chamber 52 is suppressed, and variations in the level of sterilization between the caps 33 due to the sterilant remaining on the caps 33 in the form of liquid can be prevented. In addition, the pressure in the introduction chamber 52 is maintained at a positive pressure (for example, 0 Pa or more and 200 Pa or less). As a result, the sterilant is prevented from flowing excessively into the introduction chamber 51. A first pressure gauge 73 that measures the pressure in the introduction chamber 52 is connected to the introduction chamber 52.

In the sterilant spraying chamber 53, a sterilant is sprayed onto the caps 33 conveyed along the conveyance guide 70 from the introduction chamber 52. The sterilant spraying chamber 53 is disposed below the introduction chamber 52. The sterilant is, for example, aqueous hydrogen peroxide. Spraying nozzles 81A and 81B spray the sterilant toward the caps 33 while the caps 33 roll along the conveyance guide 70 in the sterilant spraying chamber 53. A sterilant spraying device 82 is disposed above the sterilant spraying chamber 53. The sterilant spraying device 82 is connected to the spraying nozzles 81A and 81B that supply the sterilant to the caps 33.

To cause the sterilant to adhere to every region of the complex-shaped inner surfaces of the caps 33 while the caps 33 are conveyed at a high rate, the nozzle inner diameter of the spraying nozzles 81A and 81B may be φ2 mm or more and φ15 mm or less (preferably φ3 mm or more and φ10 mm or less). To prevent dripping due to a reduction in the temperature of hydrogen peroxide gas, the nozzle outer diameter of the spraying nozzles 81A and 81B may be greater than the nozzle inner diameter by 2 mm or more (preferably 4 mm or more). If the nozzle inner diameter is less than φ2 mm, there is a risk that the nozzles will be clogged due to accumulation of a stabilizer for hydrogen peroxide when the nozzles are used for a long time. The distance from the caps 33 to the distal ends of the spraying nozzles 81A and 81B is preferably 5 mm or more and 100 mm or less, more preferably 10 mm or more and 15 mm or less.

The pressure in the sterilant spraying chamber 53 is maintained at a positive pressure (for example, 0 Pa or more and 50 Pa or less), so that the sterilant is prevented from excessively flowing out of the sterilant spraying chamber 53. The amount of hydrogen peroxide discharged from the spraying nozzles 81A and 81B is preferably 50 mL/min or more and 120 mL/min or less. The amount of hydrogen peroxide to be applied to sterilize the caps 33 is 0.6 µL/cm$^2$ or more and 4.7 µL/cm$^2$ or less (preferably 1.2 µL/cm$^2$ or more and 2.4 µL/cm$^2$ or less) when the concentration is 35% by weight. When the amount of hydrogen peroxide is in this range, the caps 33 can be sterilized at a high speed, and the chemical agent can be reliably removed in an air-rinsing process described below.

FIG. 3 is a vertical sectional view of the interior of the sterilant spraying chamber 53. As illustrated in FIG. 3, in the sterilant spraying chamber 53, the conveyance guide 70 is disposed in the tubular body 59 having a tubular shape with a substantially rectangular cross section. The spraying nozzles 81A and 81B spray the sterilant toward the caps 33 conveyed along the conveyance guide 70. The spraying nozzles 81A and 81B extend inward from the top surface of the tubular body 59. The spraying nozzles 81A and 81B include the spraying nozzle 81A for the inner surfaces of the caps 33 and the spraying nozzle 81B for the outer surfaces of the caps 33. In this case, the spraying nozzles 81A and 81B spray the sterilant toward the inner and outer surfaces of each cap 33 at substantially the same timing. The sterilant spraying device 82 is provided above the sterilant spraying chamber 53. The sterilant spraying device 82 supplies the sterilant to both of the spraying nozzles 81A and 81B. In this case, the spraying nozzles 81A and 81B may be disposed at substantially the same position in the conveying direction of the caps 33. Therefore, the size of the sterilant spraying chamber 53 can be reduced.

Figure 4:
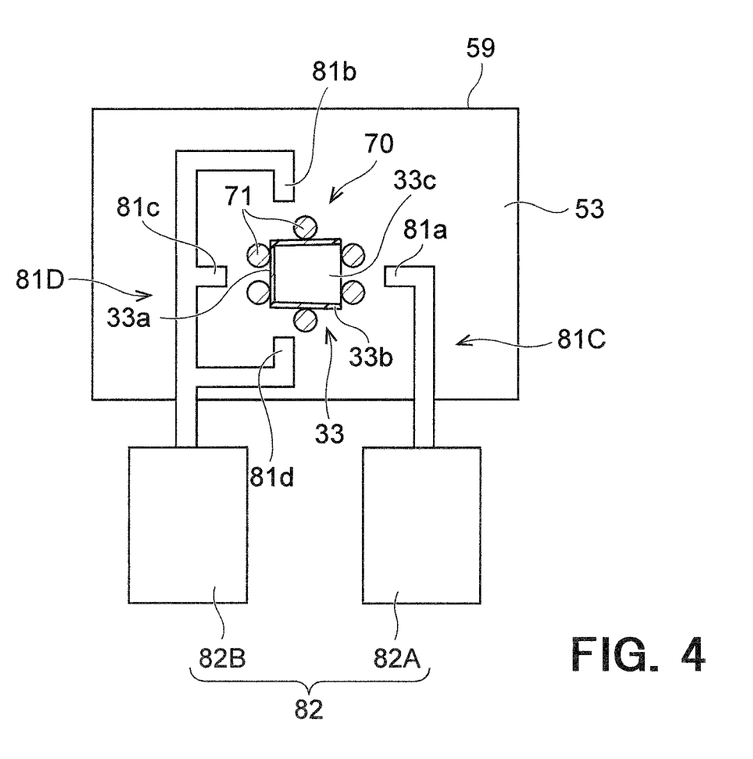
FIG. 4 is a schematic sectional view illustrating a modification of the sterilant spraying chamber included in the cap sterilization device.

FIG. 4 is a sectional view of a modification of the sterilant spraying chamber 53 at a position corresponding to that in FIG. 3. Referring to FIG. 4, the sterilant spraying device 82 includes an inner-surface sterilant spraying device 82A and an outer-surface sterilant spraying device 82B. The inner-surface sterilant spraying device 82A is connected to an inner-surface spray pipe 81C. The inner-surface spray pipe 81C includes an opening spraying nozzle 81a that sprays the sterilant toward the opening 33c of each cap 33. The outer-surface sterilant spraying device 82B is connected to an outer-surface spray pipe 81D. The outer-surface spray pipe 81D is branched into three portions, and includes an upper spraying nozzle 81b, a top-surface spraying nozzle 81c, and a lower spraying nozzle 81d. The upper spraying nozzle 81b sprays the sterilant toward an upper portion of the side surface 33b of the cap 33. The top-surface spraying nozzle 81c sprays the sterilant toward the top surface 33a of the cap 33. The lower spraying nozzle 81d sprays the sterilant toward a lower portion of the side surface 33b of the cap 33. In this case, the inner-surface sterilant spraying device 82A and the outer-surface sterilant spraying device 82B can be controlled individually. Therefore, the sterilant can be sprayed while the amounts of sterilant sprayed toward the inner and outer surfaces of the cap 33, for example, are appropriately adjusted. In addition, since the outer-surface spray pipe 81D includes the upper spraying nozzle 81b and the lower spraying nozzle 81d, the side surface 33b of the cap 33 can be sufficiently sterilized.

In addition to hydrogen peroxide, examples of the sterilant also include peracetic acid, nitric acid, chlorine-based sterilant, sodium hydroxide, potassium hydroxide, alcohols such as ethyl alcohol and isopropyl alcohol, chlorine dioxide, ozone water, acid water, and surfactants. These sterilants may be used alone, or two or more thereof may be used in combination with each other at any ratio.

Referring to FIG. 2 again, in the air-rinsing chamber 54, the caps 33 onto which the sterilant has been sprayed in the sterilant spraying chamber 53 is subjected to air-rinsing. The caps 33 are supplied from the sterilant spraying chamber 53 to the air-rinsing chamber 54 along the conveyance guide 70. Sterile hot air is blown against both the inner and outer surfaces of the caps 33 while the caps 33 are conveyed along the conveyance guide 70 in the air-rinsing chamber 54. The sterile hot air is introduced into the air-rinsing chamber 54 from the hot air supplier 80. In this case, the sterile hot air is blown against the caps 33 that are conveyed along the conveyance guide 70. The temperature of the sterile hot air (temperature at distal ends 83a of air-rinsing nozzles 83) is, for example, 80° C. or more and 140° C. or less, preferably 85° C. or more and 95° C. or less. The flow rate of the sterile hot air (flow rate of each air-rinsing nozzle 83) is, for example, 20 L/min or more and 200 L/min or less, preferably 40 L/min or more and 120 L/min or less. The time for which the sterile hot air is blown is 1 second or more and 20 seconds or less, preferably 3 seconds or more and 14 seconds or less. When the sterile hot air is blown against the caps 33, the temperature of the caps 33 is increased to 40° C. or more, preferably 50° C. or more. Thus, the sterilant that has adhered to the caps 33 is removed. The pressure in the air-rinsing chamber 54 is maintained at a positive pressure (for example, 10 Pa or more and 200 Pa or less, preferably 50 Pa or more and 150 Pa or less). The temperature and flow rate of the sterile hot air discharged from the air-rinsing nozzles 83 and the time for which the sterile hot air is blown are preferably set so that the temperature of the caps 33 in the cleaning chamber 55 is at a predetermined set temperature. The set temperature may be, for example, 50° C. or more and 150° C. or less, preferably 60° C. or more and 120° C. or less. The sterile hot air may contain a small amount of sterilant component, such as hydrogen peroxide.

Figure 5:
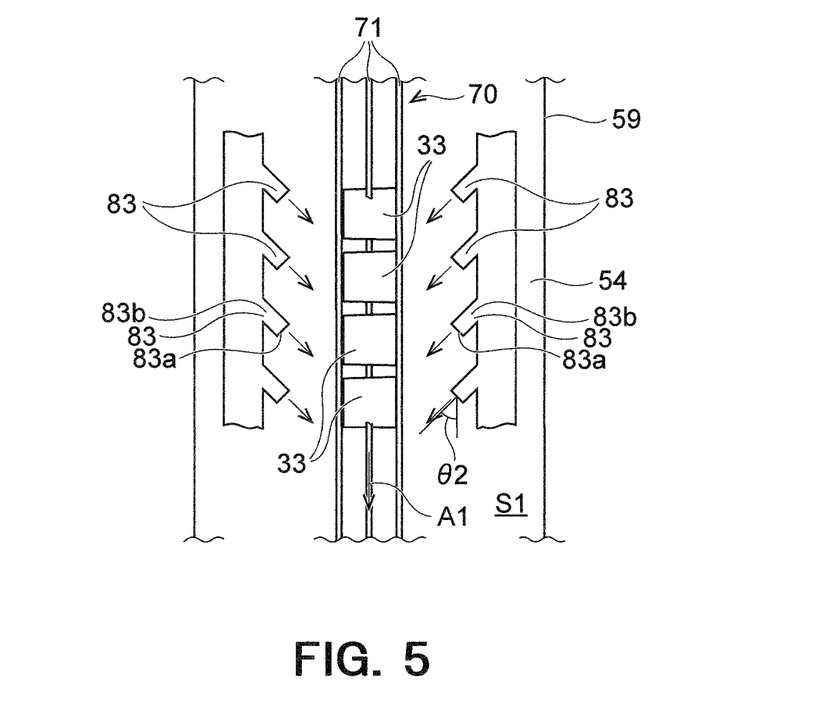
FIG. 5 is a schematic plan view of an air-rinsing chamber included in the cap sterilization device according to the embodiment (view along arrow V in FIG. 2).

FIG. 5 illustrates the interior of the air-rinsing chamber 54. As illustrated in FIG. 5, the air-rinsing nozzles 83 that supply the sterile hot air to the caps 33 are disposed in the air-rinsing chamber 54. The air-rinsing nozzles 83 are connected to the hot air supplier 80, and individually discharge the sterile hot air supplied from the hot air supplier 80. The air-rinsing nozzles 83 are disposed on both sides of the conveyance guide 70, and blow the sterile hot air against the outer and inner surfaces of the caps 33. The air-rinsing nozzles 83 for the outer surfaces of the caps 33 and the air-rinsing nozzles 83 for the inner surfaces of the caps 33 are arranged in the conveying direction of the conveyance guide 70. In this case, the sterile hot air is substantially evenly sprayed onto the inner and outer surfaces of each cap 33 by the air-rinsing nozzles 83. Thus, the air-rinsing nozzles 83 blow the sterile hot air against both the inner and outer surfaces of the caps 33 in the space inside the air-rinsing chamber 54. Therefore, the sterilant that has adhered to the inner and outer surfaces of the caps 33 in the sterilant spraying chamber 53 can be reliably removed.

Each air-rinsing nozzle 83 is disposed such that the distal end 83a thereof is in front of a proximal end 83b thereof in the conveying direction of the conveyance guide 70 (direction of arrow A1 in FIG. 5). The sterile hot air is discharged from the distal ends 83a of the air-rinsing nozzles 83. Therefore, the sterile hot air discharged from the air-rinsing nozzles 83 is supplied toward the center of the conveyance guide 70 in the width direction and forward in the conveying direction of the conveyance guide 70. Accordingly, the sterile hot air serves not only to remove the sterilant that has adhered to the inner and outer surfaces of the caps 33 but also to convey the caps 33 forward in the conveying direction by the pressure thereof. Thus, the sterile hot air serves to increase the propulsion force, which would be insufficient if the caps 33 are moved along the guide 70 only by their own weight, and the caps 33 can be smoothly moved along the conveyance guide 70.

The view of FIG. 5 is viewed in a direction normal to a plane S1 on which the conveyance guide 70 is disposed. When viewed in the direction normal to the plane S1, an angle θ2 between each air-rinsing nozzle 83 and the conveying direction of the conveyance guide 70 is preferably 10° or more and 80° or less, more preferably 20° or more and 70° or less, and still more preferably 30° or more and 60° or less. When the angle θ2 is 10° or more, the sterile hot air is reliably blown against the caps 33, and the sterilant that has adhered to the caps 33 can be reliably removed. When the angle θ2 is 80° or less, a sufficient propulsion force can be applied to the caps 33. The air-rinsing nozzles 83 may be bent in a V-shape when viewed in the direction normal to the plane S1.

The total number of air-rinsing nozzles 83 disposed in the air-rinsing chamber 54 (total number of air-rinsing nozzles 83 disposed adjacent to the inner and outer surfaces of the caps 33) is preferably 10 or more and 300 or less. The inner diameter of the distal ends 83a of the air-rinsing nozzles 83 is preferably φ3 mm or more and φ10 mm or less. The minimum distance from the distal ends 83a of the air-rinsing nozzles 83 to the caps 33 (distance in a direction perpendicular to the conveying direction of the conveyance guide 70) is preferably 20 mm or more and 30 mm or less.

Referring to FIG. 2, in the cleaning chamber 55, the caps 33 that have been subjected to air-rinsing in the air-rinsing chamber 54 are cleaned. The caps 33 are supplied from the air-rinsing chamber 54 to the cleaning chamber 55 along the conveyance guide 70. The caps 33 are conveyed along the conveyance guide 70 in the cleaning chamber 55. While the caps 33 are being conveyed, first, a cleaning nozzle 84 sprays cleaning liquid, such as sterile water, against the inner and outer surfaces of the caps 33. Accordingly, even if foreign matter has adhered to the caps 33, the foreign matter can be reliably removed. In addition, the caps 33 that have been heated by the sterile hot air can be cooled. Next, an air blow nozzle 85 blows sterile air against the inner and outer surfaces of the caps 33 to remove the cleaning liquid, such as sterile water, that has adhered to the caps 33. Even after the sterile air is blown against the caps 33, a small amount of sterile water remains on the caps 33. Accordingly, while the caps 33 are being conveyed along the conveyance guide 70, appropriate lubrication is provided between the conveyance guide 70 and the caps 33 to prevent an increase in the temperature of the caps 33 due to heat of friction between the conveyance guide 70 and the caps 33. Since an increase in the temperature of the caps 33 is suppressed, the caps 33 can be reliably attached by the cap attaching device 16. A second pressure gauge 74 that measures the pressure in the cleaning chamber 55 is connected to the cleaning chamber 55. The pressure in the cleaning chamber 55 is maintained at a positive pressure (for example, 50 Pa or more and 200 Pa or less). The pressure in the cleaning chamber 55 is preferably higher than the pressures in the introduction chamber 52 and the air-rinsing chamber 54. Accordingly, atmosphere containing the sterilant is prevented from flowing out toward the cap attaching device 16. In the present embodiment, it is not necessary that the cleaning chamber 55 be provided. In addition, when a lubricant is applied to the caps 33, such as when carbonated beverage caps are used as the caps 33, the cleaning nozzle 84 may be temporarily stopped to prevent separation of the lubricant. An advantage of sterilizing and cleaning the caps 33 on the conveyance guide 70 is that the sterile water used in the final cleaning step is not dispersed into the air-rinsing chamber 54 on the upstream side. It is not necessary that the cleaning nozzle 84 for cleaning with the sterile water be provided.

A full sensor 86 is provided on the conveyance guide 70 in the cleaning chamber 55. The full sensor 86 detects an accumulation of the caps 33 on the conveyance guide 70. When the full sensor 86 detects that the caps 33 have accumulated, a controller (not illustrated) controls the cap movement controller 72 to stop the movement of the caps 33. Thus, the number of caps 33 conveyed to the chambers 52, 53, 54, and 55 can be controlled.

The structure of the hot air supplier 80 will now be described. The hot air supplier 80 includes a blower 87, a high efficiency particulate air (HEPA) filter 88, and an electric heater 89. The blower 87 feeds air to the HEPA filter 88, and the HEPA filter 88 removes impurities from the air to produce sterile air. The sterile air is heated by the electric heater 89, so that sterile hot air in a predetermined temperature range is obtained. The sterile hot air is supplied to the introduction chamber 52, the air-rinsing chamber 54, and the cleaning chamber 55 successively through a main air pipe 91a and air pipes 91b to 91d that branch from the main air pipe 91a. A temperature controller 92 and a flow rate controller 93 are disposed in the main air pipe 91a. The temperature controller 92 controls the temperature of the sterile hot air in the main air pipe 91a. The flow rate controller 93 controls the flow rate of the sterile hot air in the main air pipe 91a. Regulating valves 94 for regulating the supply air pressures in the air pipes 91b to 91d are disposed at intermediate positions of the air pipes 91b to 91d. The hot air supplier 80 may use compressed air instead of blower air.

Exhaust pipes 95a to 95c are connected to the introduction chamber 52, the air-rinsing chamber 54, and the cleaning chamber 55. Gas is discharged from the introduction chamber 52, the air-rinsing chamber 54, and the cleaning chamber 55 through the exhaust pipes 95a to 95c. The exhaust pipes 95a to 95c are connected to a blower 96 that sucks gas from the exhaust pipes 95a to 95c, and a scrubber 97 that processes a sterilant component in the gas is connected to the blower 96. Regulating valves 98 for regulating the exhaust pressures in the exhaust pipes 95a to 95c are disposed at intermediate positions of the exhaust pipes 95a to 95c.

In this case, an exhaust pressure E4 in the air-rinsing chamber 54 is higher than an exhaust pressure E2 in the introduction chamber 52. Accordingly, even when the sterile hot air is supplied to the air-rinsing chamber 54 at a high flow rate, air can be sucked from the air-rinsing chamber 54 to prevent an excessive increase in the pressure in the air-rinsing chamber 54.

In addition, an exhaust pressure E5 in the cleaning chamber 55 is higher than the exhaust pressure E2 in the introduction chamber 52. Accordingly, gas containing the sterilant can be strongly sucked from the cleaning chamber 55, so that atmosphere containing the sterilant can be prevented from flowing out toward the cap attaching device 16.

It is not necessary that gas be discharged from the sterilant spraying chamber 53 (exhaust pressure may be 0). Accordingly, gas containing the sterilant does not accumulate in the introduction chamber 52, and condensation of the gas containing the sterilant in the introduction chamber 52 can be prevented. When gas is not discharged from the sterilant spraying chamber 53, the sterilant concentration in the atmosphere in the sterilant spraying chamber 53 can be increased, so that the caps 33 can be reliably sterilized in the sterilant spraying chamber 53. In addition, when the sterilant concentration is increased in the sterilant spraying chamber 53, the caps 33 can be reliably sterilized even when the caps 33 is conveyed at a high rate.

To summarize the above discussion, E5>E2 and E4>E2 are satisfied. The relationship between the magnitudes of E5 and E4 is not limited. When the degree of positive pressure in the cap sterilization device 50 is greater than the degree of positive pressure in a capper portion of a filling chamber of the filling device 20, the conveyance of the caps 33 can be improved. More specifically, the degree of positive pressure in the cap sterilization device 50 may be greater than the degree of positive pressure in the filling chamber by 30 Pa or more and 200 Pa or less. When the pressure difference is 200 Pa or more, there is a risk that the sterilant gas (hydrogen peroxide) will flow into the filling chamber from the cap sterilization device 50 and that the sterilant will be dissolved into product liquid at a filling valve opening.

Throughout the cap sterilization device 50, the conveyance rate of the caps 33 is 100 cpm or more and 1500 cpm or less, preferably 500 cpm or more and 1000 cpm or less. According to the cap sterilization device 50 of the present embodiment, the caps 33 can be reliably sterilized even when the caps 33 are conveyed at such a high rate. Here, cpm (caps per minute) is the number of caps 33 that pass a certain position in one minute. When a filling rate at which each bottle 30 is filled is low, such as when the bottles 30 are large (with an inner capacity of 1 L of more), the conveyance rate of the caps 33 can be reduced from the above-described rate in accordance with the filling rate. In such a case, conditions (temperature, flow rate, etc.) under which the hot air is supplied to the introduction chamber 52 and the air-rinsing chamber 54 may be adjusted to prevent an increase in the temperature of the caps 33.

(Content Filling Method)

A content filling method using the above-described content filling system 10 (FIG. 1) will now be described. In the following description, a filling method in an ordinary state, more specifically, a content filling method for filling the bottles 30 with a content, such as a beverage, to produce the product bottles 35 will be described.

First, the bottles 30 in an empty state are successively supplied to the bottle supplying unit 21 from the outside of the content filling system 10. The bottles 30 are conveyed from the bottle supplying unit 21 to the sterilization device 11 by one of the conveying wheels 12 (container supplying step).

Next, the sterilization device 11 sterilizes the bottles 30 by using an aqueous hydrogen peroxide solution, which serves as a sterilant (bottle sterilization step). The aqueous hydrogen peroxide solution is gas or mist obtained by temporarily vaporizing the aqueous hydrogen peroxide solution having a concentration of 1% by weight or more, preferably 35% by weight, and then condensing the vapor. The gas or mist is supplied to the bottles 30.

Subsequently, the bottles 30 are conveyed to the air-rinsing device 14 by another one of the conveying wheels 12. The air-rinsing device 14 supplies sterile heated air or room temperature air to activate the hydrogen peroxide and remove foreign matter, the hydrogen peroxide, etc. from the bottles 30 at the same time. Next, the bottles 30 are conveyed to the sterile-water-rinsing device 15 by another one of the conveying wheels 12. The sterile-water-rinsing device 15 performs cleaning using sterile water at 15° C. to 85° C. (rinsing step). More specifically, the sterile water at 15° C. to 85° C. is introduced into the bottles 30 at a flow rate of 5 L/min or more and 15 L/min or less. At this time, preferably, the bottles 30 are inverted, and the sterile water is introduced into the bottles 30 from the mouths that face downward. The sterile water flows out of the bottles 30 through the mouths. The sterile water is used to rinse off the hydrogen peroxide that has adhered to the bottles 30 and remove the foreign matter. The step of introducing the sterile water into the bottles 30 is not necessarily performed.

Subsequently, the bottles 30 are conveyed to the filling device 20 by another one of the conveying wheels 12. The filling device 20 fills the bottles 30 with the content through the mouths of the bottles 30 while rotating (revolving) the bottles 30 (filling step). The filling device 20 fills the sterilized bottles 30 with the content at a room temperature after the content, which is prepared in advance, is subjected to a heat sterilization process and cooled to the room temperature.

Subsequently, the bottles 30 filled with the content are conveyed to the cap attaching device 16 by another one of the conveying wheels 12.

The caps 33 are sterilized by the cap sterilization device 50 illustrated in FIG. 2 in advance (cap sterilization step). In this step, first, a large number of caps 33 are randomly charged into the hopper 56 from the outside of the cap sterilization device 50. Next, the caps 33 that have been randomly charged into the hopper 56 are aligned by the sorter 57, and then conveyed to the cap inspection device 58. Next, the cap inspection device 58 inspects the shape, for example, of each cap 33. The caps 33 that have passed the inspection are conveyed toward the cap introduction unit 51 in a line.

The cap movement controller 72 controls the movement of the caps 33 introduced into the cap introduction unit 51. For example, first, the cap movement controller 72 temporarily stops the movement of the caps 33 so that the caps 33 accumulate on the conveyance guide 70. Then, when the number of caps 33 that have accumulated reaches a certain number, the cap movement controller 72 may be opened to start the movement of the caps 33. Accordingly, the caps 33 are conveyed to the introduction chamber 52 along the conveyance guide 70 by their own weight. Next, the caps 33 are conveyed along the conveyance guide 70 by their own weight in the introduction chamber 52, and enter the sterilant spraying chamber 53. Next, in the sterilant spraying chamber 53, the spraying nozzles 81A and 81B spray the sterilant, such as aqueous hydrogen peroxide, onto the caps 33 while the caps 33 are conveyed along the conveyance guide 70. Thus, the inner and outer surfaces of the caps 33 are sterilized.

Subsequently, the caps 33 onto which the sterilant has been sprayed are conveyed to the air-rinsing chamber 54. In the air-rinsing chamber 54, the caps 33 are conveyed along the conveyance guide 70 by their own weight. While the caps 33 are being conveyed, the air-rinsing nozzles 83 disposed on both sides of the conveyance guide 70 blow sterile hot air against the inner and outer surfaces of the caps 33. Thus, air-rinsing is performed to rinse off the sterilant that has adhered to the caps 33. In the present embodiment, each air-rinsing nozzle 83 is disposed such that the distal end 83a thereof is in front of the proximal end 83b thereof in the conveying direction of the conveyance guide 70 (direction of arrow A1 in FIG. 5). Accordingly, the sterile hot air serves not only to remove the sterilant that has adhered to the inner and outer surfaces of the caps 33 but also to increase the propulsion force, which would be insufficient if the caps 33 are moved along the guide 70 only by their own weight. Therefore, the caps 33 can be smoothly moved along the conveyance guide 70.

Next, the caps 33 are conveyed from the air-rinsing chamber 54 to the cleaning chamber 55. In the cleaning chamber 55, the cleaning nozzle 84 sprays cleaning liquid, such as sterile water, against the caps 33 while the caps 33 are conveyed along the conveyance guide 70 by their own weight, so that foreign matter, for example, that has adhered to the caps 33 is removed and that the caps 33 are cooled. Subsequently, the air blow nozzle 85 blows sterile air against the caps 33 to remove the sterile water. At this time, the sterile water that has adhered to the caps 33 is not entirely removed, and a portion thereof remains on the caps 33. Accordingly, the temperature of the caps 33 is prevented from being increased due to the heat of friction between the conveyance guide 70 and the caps 33, so that the caps 33 can be reliably attached by the cap attaching device 16. Since the amount of sterile water that remains on the caps 33 is small, the remaining sterile water is removed by, for example, the above-described heat of friction before the caps 33 reach the cap attaching device 16.

After that, the caps 33 are conveyed out of the cleaning chamber 55 and to the cap attaching device 16 along the conveyance guide 70.

Referring to FIG. 1 again, the cap attaching device 16 attaches the caps 33 that haven been sterilized by the cap sterilization device 50 as described above to the mouths of the bottles 30 conveyed from the filling device 20. Thus, the product bottles 35 including the bottles 30 and the caps 33 are obtained (cap attaching step).

After that, the product bottles 35 are conveyed from the cap attaching device 16 to the product bottle carry-out unit 22, and are conveyed to the outside of the content filling system 10.

The above-described steps from the sterilization step to the cap attaching step are performed in a sterile atmosphere, that is, in a sterile environment, in the sterile chamber 13. After the sterilization process, sterile air at a positive pressure is supplied into the sterile chamber 13 so that sterile air continuously flows out of the sterile chamber 13.

The production (conveyance) rate of the bottles 30 in the content filling system 10 is preferably 100 bpm or more and 1500 bpm or less. Here, bpm (bottles per minute) corresponds to the conveyance rate of the bottles 30 in one minute.

As described above, according to the present embodiment, the conveyance guide 70 is disposed to extend successively through the cap introduction unit 51, the introduction chamber 52, the sterilant spraying chamber 53, the air-rinsing chamber 54, and the cleaning chamber 55. The caps 33 are conveyed along the conveyance guide 70 by their own weight from the cap introduction unit 51 and the introduction chamber 52 toward the air-rinsing chamber 54 and the cleaning chamber 55. Thus, the caps 33 can be conveyed along the conveyance guide 70, which is inclined, without using a driving device for conveying the caps 33.

In addition, according to the present embodiment, the air-rinsing nozzles 83 that supply hot air to the caps 33 are disposed in the air-rinsing chamber 54. Each air-rinsing nozzle 83 is disposed such that the distal end 83a thereof is in front of the proximal end 83b thereof in the conveying direction of the conveyance guide 70. Accordingly, the sterile hot air serves not only to remove the sterilant that has adhered to the caps 33 but also to increase the propulsion force, which would be insufficient if the caps 33 are moved along the guide 70 only by their own weight. As a result, the conveyance rate at which the caps 33 are conveyed along the conveyance guide 70 can be increased.

In particular, even when the pressure in the cleaning chamber 55 is higher than the pressures in the introduction chamber 52 and the air-rinsing chamber 54 and when air flows from the cleaning chamber 55 toward the air-rinsing chamber 54, a deficiency in the propulsion force for the caps 33 can be compensated for by the sterile hot air from the air-rinsing nozzles 83.

In addition, according to the present embodiment, the air-rinsing nozzles 83 are disposed on both sides of the conveyance guide 70. Accordingly, the sterile hot air is blown against both the inner and outer surfaces of the caps 33 by the air-rinsing nozzles 83, and the sterilant that has been sprayed onto the inner and outer surfaces of the caps 33 by the spraying nozzles 81A and 81B in the sterilant spraying chamber 53 can be reliably removed. Therefore, a high concentration sterilant can be sprayed onto the caps 33 by the spraying nozzles 81A and 81B. As a result, the conveyance rate of the caps 33 can be increased. In addition, the propulsion force can be evenly applied to the inner and outer surfaces of the caps 33 by the sterile hot air discharged from the air-rinsing nozzles 83.

In addition, according to the present embodiment, the cap sterilization device 50 is sectioned into the chambers 52, 53, 54, and 55, and the pressure is controlled in each of the chambers 52, 53, 54, and 55. Therefore, the caps 33 can be reliably sterilized while being conveyed at a high rate in the cap sterilization device 50.

In addition, according to the present embodiment, the cleaning nozzle 84 sprays the cleaning liquid, such as sterile water, against the caps 33 in the cleaning chamber 55 to clean the caps 33. Accordingly, foreign matter that has adhered to the caps 33 can be reliably removed. In addition, the caps 33 heated by the sterile hot air can be cooled. Therefore, even when the caps 33 are conveyed at a high rate, an increase in the temperature of the caps 33 due to heat of friction between the conveyance guide 70 and the caps 33 can be prevented. As a result, the conveyance rate of the caps 33 can be increased.

In addition, according to the present embodiment, the air blow nozzle 85 blows sterile air against the caps 33 in the cleaning chamber 55 to remove the cleaning liquid that has adhered to the caps 33. Thus, most of the cleaning liquid, such as sterile water, that has adhered to the caps 33 is removed. Therefore, the caps 33 can be prevented from being conveyed to the cap attaching device 16 while the sterile water, for example, remains thereon.

In addition, according to the present embodiment, a small amount of cleaning liquid, such as sterile water, remains on the caps 33 even after the sterile air has been blown against the caps 33 by the air blow nozzle 85. Accordingly, while the caps 33 are being conveyed along the conveyance guide 70 from the cleaning chamber 55 toward the cap attaching device 16, appropriate lubrication is provided between the conveyance guide 70 and the caps 33 to prevent an increase in the temperature of the caps 33 due to heat of friction between the conveyance guide 70 and the caps 33. Since an increase in the temperature of the caps 33 is suppressed, the caps 33 can be reliably attached by the cap attaching device 16. In the cap attaching device 16, sterile air may be blown against the inner surfaces of the caps 33 to remove cleaning water that remains in the caps 33. Thus, mixture of the cleaning water into the bottles 30 can be minimized.

Thus, even when the conveyance rate of the caps 33 in the cap sterilization device 50 is as high as 100 cpm or more and 1500 cpm, the caps 33 can be reliably sterilized without causing leakage of the sterilant from the housing 60.

In addition, according to the present embodiment, the caps 33 can be sterilized by using a system obtained by renovating known equipment (for example, a chute). Therefore, the known equipment may be efficiently used.

Figure 6:
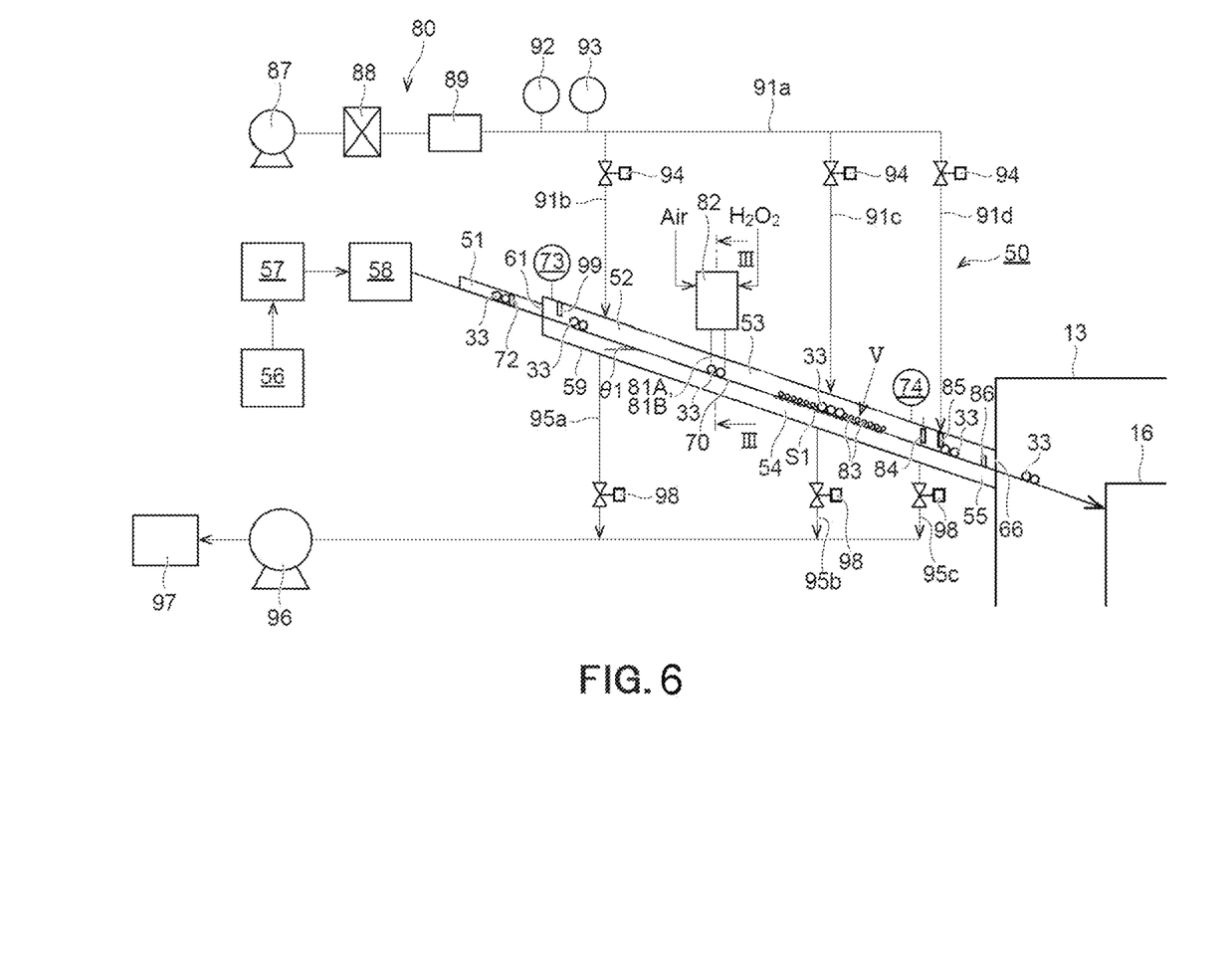
FIG. 6 is a schematic front view of a cap sterilization device according to a modification.

As illustrated in FIG. 6, the interiors of the chambers 52, 53, 54, and 55 may be cleaned and sterilized by using an upstream nozzle 99 disposed in the introduction chamber 52, in which resin powder and the stabilizer of the sterilant (hydrogen peroxide) easily accumulate. More specifically, the upstream nozzle 99 that discharges sterilant or cleaning liquid may be provided in the introduction chamber 52, so that the sterilant or cleaning liquid discharged from the upstream nozzle 99 flows along the inclined bottom surface of each of the chambers 52, 53, 54, and 55 to successively sterilize or clean the introduction chamber 52, the sterilant spraying chamber 53, the air-rinsing chamber 54, and the cleaning chamber 55. In this case, the sterilant (peracetic acid) or sterile water sprayed from the upstream nozzle 99 may flow through the air-rinsing chamber 54 and the cleaning chamber 55 at a downstream location and clean the cap attaching device (capper, a closing-and-capping machine) 16.

The amount of foreign matter in the air-rinsing chamber 54 and the cleaning chamber 55 can be reduced by causing the sterilant (hydrogen peroxide or peracetic acid) or sterile water to flow through the air-rinsing nozzles 83, the cleaning nozzle 84, and/or the air blow nozzle 85.

The components of the above-described embodiment and modifications may be applied in combination with each other as necessary. Also, some of the components of the above-described embodiment and modifications may be omitted.

The invention claimed is:

1. A cap sterilization device comprising:
an introduction unit;
a sterilant spraying unit that sprays a sterilant onto a cap supplied from the introduction unit;
an air-rinsing unit that subjects the cap onto which the sterilant has been sprayed by the sterilant spraying unit to air-rinsing;
a cleaning unit that cleans the cap that has been subjected to air-rinsing in the air-rinsing unit; and
a conveyance guide that is disposed to extend successively through the introduction unit, the sterilant spraying unit, the air-rinsing unit, and the cleaning unit and along which the cap is conveyed from the introduction unit toward the cleaning unit,
wherein the air-rinsing unit is provided with an air-rinsing nozzle that supplies hot air to the cap, the air-rinsing nozzle being disposed with a distal end of the air-rinsing nozzle in front of a proximal end of the air-rinsing nozzle in relation to a conveying direction of the conveyance guide,
the cap is conveyed along the conveyance guide by its own weight from the introduction unit toward the cleaning unit through the sterilant spraying unit,
the introduction unit is provided with a cap movement controller that controls a movement of the cap along the conveyance guide,
when the cap movement controller temporarily stops the cap on the conveyance guide, a plurality of caps accumulate on the conveyance guide in a region above the cap movement controller, then, when the cap movement controller is opened, the caps that have accumulated pass the cap movement controller and move toward the introduction chamber,
a sensor is provided on the conveyance guide at a location above the cap movement controller, and the sensor is used to determine a number of the plurality of caps that have accumulated on the conveyance guide,
a full sensor is provided on the conveyance guide in the cleaning unit, the full sensor detects an accumulation of the cap on the conveyance guide, and
when the full sensor detects that the cap has accumulated, the movement of the cap is stopped by the cap movement controller.

2. The cap sterilization device according to claim 1, wherein a plurality of air-rinsing nozzles are provided, and the air-rinsing nozzles are disposed on each side of the conveyance guide.

3. The cap sterilization device according to claim 1, wherein an angle between the air-rinsing nozzle and the conveying direction of the conveyance guide is 10° or more and 80° or less when viewed in a direction normal to a plane on which the conveyance guide is disposed.

4. The cap sterilization device according to claim 1, wherein the cap is conveyed at a conveyance rate of 100 caps per minute or more and 1500 caps per minute or less.

5. A content filling system comprising the cap sterilization device according to claim 1.

* * * * *